US010875900B2

(12) United States Patent
Miyakawa et al.

(10) Patent No.: US 10,875,900 B2
(45) Date of Patent: Dec. 29, 2020

(54) PEPTIDE DERIVED FROM GPC3, PHARMACEUTICAL COMPOSITION FOR TREATMENT OR PREVENTION OF CANCER USING SAME, IMMUNITY INDUCER, AND METHOD FOR PRODUCING ANTIGEN-PRESENTING CELLS

(71) Applicant: Cytlimic Inc., Tokyo (JP)

(72) Inventors: Tomoya Miyakawa, Tokyo (JP); Masaaki Oka, Yamaguchi (JP); Shoichi Hazama, Yamaguchi (JP); Koji Tamada, Yamaguchi (JP); Keiko Udaka, Kochi (JP)

(73) Assignee: Cytlimic Inc., Tokyo (JP)

( * ) Notice: Subject to any disclaimer, the term of this patent is extended or adjusted under 35 U.S.C. 154(b) by 0 days.

(21) Appl. No.: 16/782,544

(22) Filed: Feb. 5, 2020

(65) Prior Publication Data

US 2020/0157163 A1    May 21, 2020

Related U.S. Application Data

(62) Division of application No. 16/185,734, filed on Nov. 9, 2018, now Pat. No. 10,590,179, which is a division of application No. 15/556,694, filed as application No. PCT/JP2016/057356 on Mar. 9, 2016, now Pat. No. 10,526,388.

(30) Foreign Application Priority Data

Mar. 9, 2015 (JP) ................. 2015-046463

(51) Int. Cl.
*A61P 35/00* (2006.01)
*C07K 14/47* (2006.01)
*A61K 38/00* (2006.01)
*A61K 39/00* (2006.01)
*C07K 14/705* (2006.01)
*A61P 37/04* (2006.01)

(52) U.S. Cl.
CPC .......... *C07K 14/4748* (2013.01); *A61K 38/00* (2013.01); *A61K 39/00* (2013.01); *A61K 39/0011* (2013.01); *A61P 35/00* (2018.01); *A61P 37/04* (2018.01); *C07K 14/705* (2013.01); *A61K 2039/572* (2013.01)

(58) Field of Classification Search
None
See application file for complete search history.

(56) References Cited

U.S. PATENT DOCUMENTS

| | | |
|---|---|---|
| 5,196,523 A | 3/1993 | Lee |
| 2002/0192195 A1 | 12/2002 | Triebel |
| 2007/0081991 A1 | 4/2007 | Soderstrom |
| 2007/0087009 A1 | 4/2007 | Burdin et al. |
| 2009/0035330 A1 | 2/2009 | Dewerchin |
| 2009/0123460 A1 | 5/2009 | Noelle et al. |
| 2009/0155308 A1 | 6/2009 | Moon et al. |
| 2009/0239806 A1 | 9/2009 | Nishimura et al. |
| 2010/0015101 A1 | 1/2010 | Sato et al. |
| 2010/0028373 A1 | 2/2010 | Fujioka et al. |
| 2011/0028403 A1 | 2/2011 | Le Poole et al. |
| 2013/0217122 A1 | 8/2013 | Kaplan |
| 2015/0023992 A1 | 1/2015 | Sette et al. |
| 2018/0071362 A1 | 3/2018 | Miyakawa et al. |

FOREIGN PATENT DOCUMENTS

| | | |
|---|---|---|
| CA | 2963909 A | 4/2016 |
| CN | 101568550 A | 10/2009 |
| EP | 1002108 | 5/2000 |
| EP | 1750707 | 2/2007 |
| EP | 2214705 | 8/2010 |
| EP | 2214705 B1 | 8/2010 |
| EP | 2572715 A1 | 3/2013 |
| JP | 08-151396 A | 6/1996 |
| JP | 2001-510806 A | 8/2001 |
| JP | 2006-512391 A | 4/2006 |
| JP | 2007-514725 A | 6/2007 |
| JP | 2008-540625 A | 11/2008 |
| JP | 2010-538655 A | 12/2010 |
| JP | 2011-506309 A | 3/2011 |
| RU | 2333767 C2 | 10/2007 |
| RU | 2709015 C2 | 4/2019 |
| WO | WO 99/04810 A2 | 2/1999 |
| WO | WO 2004/018667 A1 | 3/2004 |
| WO | WO 2005/060966 A1 | 7/2005 |
| WO | WO 2007/018199 A1 | 2/2007 |
| WO | WO 2007/119515 A1 | 10/2007 |
| WO | WO 2008/106491 A2 | 9/2008 |
| WO | WO 2009/072767 A2 | 6/2009 |
| WO | WO 2011/044246 A1 | 4/2011 |
| WO | WO 2013/119863 A1 | 8/2013 |
| WO | WO 2013/143026 A1 | 10/2013 |
| WO | WO 2014/134355 A1 | 9/2014 |
| WO | WO 2016/056596 A1 | 10/2015 |
| WO | WO 2015/168379 A2 | 11/2015 |

(Continued)

OTHER PUBLICATIONS

Office Action dated Mar. 17, 2020, in AU 2016244570.
International Search Report dated Nov. 24, 2015, in PCT/JP2015/078504.
International Search Report dated Jun. 14, 2016, in PCT/JP2016/057356.
International Search Report dated Jun. 28, 2016, in PCT/JP2016/061463.

(Continued)

*Primary Examiner* — Fred H Reynolds
(74) *Attorney, Agent, or Firm* — Foley & Lardner LLP

(57) ABSTRACT

The present invention provides a peptide containing 8 or more consecutive amino acid residues in an amino acid sequence of any of SEQ ID NOS: 1 to 11 and consisting of 11 or less amino acid residues.

8 Claims, 4 Drawing Sheets

Specification includes a Sequence Listing.

(56) References Cited

FOREIGN PATENT DOCUMENTS

| WO | WO 2016/143816 A1 | 9/2016 |
|---|---|---|
| WO | WO 2016/163489 A1 | 10/2016 |

OTHER PUBLICATIONS

International Search Report dated Jun. 27, 2017, in PCT/JP2017/015227.

AdipoGen™ Safety Data Sheet, "LAG-3 (mouse):Fc mMouse) (rec)," May 5, 2011, 3 pages.

American Cancer Society, "Non-specific cancer immunotherapies and adjuvants," Aug. 8, 2016, 4 pages.

Brignone et al., "A Soluble Form of Lymphocyte Activation Gene-3 (IMP321) Induces Activation of a Large Range of Human Effector Cytotoxic Cells," The Journal of Immunology, 2007, 179:4202-4211.

Faure et al., "Inducible Hsp70 as Target of Anticancer Immunotherapy: Identification of HLA-A*0201-Restricted Epitopes," Int. J. Cancer, Mar. 1, 2004, 108(6):863-870.

Galluzzi et al., "Trial Watch: Experimental Toll-like receptor agonists for cancer therapy," OncoImmunology, Aug. 1, 2012, 1(5):699-739.

Iwama et al., "Identification of an $H2-K^b$ or $H2-D^b$ restricted and glypican-3-derived cytotoxic T-lymphocyte epitope peptide," International Journal of Oncology, Jan. 23, 2013, 42(3):831-838.

Kano et al., "Combined adjuvants of poly(I:C) plus LAG-3-Ig improve antitumor effects of tumor-specific T cells, preventing their exhaustion," Cancer Sci., Apr. 15, 2016, 107(4):398-406.

Komori et al., "Identification of HLA-A2- or HLA-A24-Restricted CTL Epitopes Possibly Useful for Glypican-3-Specific Immunotherapy of Hepatocellular Carcinoma," Clin. Cancer Res., May 1, 2006, 12(9):2689-2697.

Nakatsura et al., "Mouse Homologue of a Novel Human Oncofetal Antigen, Glypican-3, Evokes T-Cell-Mediated Tumor Rejection without Autoimmune Reactions in Mice," Clinical Cancer Research, Dec. 15, 2004, 10(24):8630-8640.

Okochi et al., "Identification of HLA-A24-Restricted Epitopes with High Affinities to Hsp70 Using Peptide Arrays," Journal of Bioscience and Bioengineering, Mar. 2008, 105(3):198-203.

Reed et al., "New horizons in adjuvants for vaccine development," Trends in Immunology, Dec. 6, 2008, 30(1):23-32.

Romano et al., "MART-1 peptide vaccination plus IMP321 (LAG-3Ig fusion protein) in patients receiving autologous PBMCs after lymphodepletion: results of a Phase I trial," Journal of Translational Medicine, Apr. 12, 2014, 12(97):1-12.

Sierro et al., "The CD4-like molecule LAG-3, biology and therapeutic applications," Expert Opin. On Ther. Targets, Jan. 2011, 15(1):91-101.

Udaka et al., "An automated prediction of MHC class I-binding peptides based on positional scanning with peptide libraries," Immunogenetics, Jul. 8, 2000, 51(10):816-828.

Vacchelli et al., "Trial Watch: Toll-like receptor agonists for cancer therapy," OncoImmunology, Aug. 1, 2013, 2(8):e25238, 14 pages.

Wick et al., "Profound CD8+ T cell immunity elicited by sequential daily immunization with exogenous antigen plus the TLR3 agonist poly(I:C)," Vaccine, 2011, 29:984-993.

Supplementary Partial European Search Report dated Apr. 13, 2018, in EP 15849707.3.

Office Action dated Mar. 23, 2018, in Russian Application No. RU 2017115719, with English translation.

Pan et al., "Interferon-γ is an autocrine mediator for dendritic cell maturation," Immunology Letters, May 26, 2004, 94(1-2):141-151.

Supplemental European Search Report dated Jul. 11, 2018, in EP 15849707.3.

Supplementary European Search Report dated Nov. 16, 2018, in EP 16776655.9.

Office Action dated Dec. 5, 2018, in U.S. Appl. No. 15/516,918.

Fougeray et al., "A soluble LAG-3 protein as an immunopotentiator for therapeutic vaccines: Preclinical evaluation of IMP321," Vaccine, Jun. 29, 2006, 24(26):5426-5433.

Fransen et al., "Local immunomodulation for cancer therapy," OncoImmunology, Nov. 1, 2013, 2(11):e26493, 3 pages.

Goldberg et al., "LAG-3 in Cancer Immunotherapy," Curr. Top. Microbiol. Immunol., Jan. 1, 2011, 344:269-278.

Harig et al., "Induction of cytotoxic T-cell responses against immunoglobulin V region-derived peptides modified at human leukocyte antigen-A2 binding residues," Blood, Nov. 15, 2001, 98(10):2999-3005.

Office Action dated Jan. 28, 2019, in U.S. Appl. No. 15/556,694.

P.H.N. Celie et al., "Crystal structure of MHC CLass I HLA-A2.1 bound to HIV-1 envelope peptide env120-128," RSCB Protein Data Bank, 2010, https://www.rcsb.org/structure/2X4O, 6 pages.

Ammi et al., "Poly(I:C) as cancer vaccine adjuvant: Knocking on the door of medical breakthroughs," Pharmacology & Therapeutics, 2015, vol. 146, pp. 120-131.

Office Action dated Jun. 17, 2019, in U.S. Appl. No. 15/564,604.

Office Action dated Aug. 29, 2019, in RU 201735038, with English translation.

Office Action dated Sep. 20, 2019, in RU 2017134693, with English translation.

Ebner et al., "Identification of Multiple T Cell Epitopes on Bet v I, the Major Birch Pollen Allergen, Using Specific T Cell Clones and Overlapping Peptides," The Journal of Immunology, Feb. 1, 1993, 150(3):1047-1054.

Guha, Malini, "Anticancer TLR agonists on the ropes," Nature Reviews Drug Discovery, Jul. 2012, 11(7):503-505.

Jiang et al., "Expression significance of HLA-DR antigen and heat shock protein 70 in hepatocellular carcinoma," World Chinese Journal of Digestology, Oct. 15, 2001, 9(10):1139-1142, with English abstract.

Office Action dated May 19, 2020, in RU 2019113989, with English translation.

Office Action dated May 28, 2020, in CN 201580054234.7, with English translation.

Sabbatini et al., "Phase I Trial of Overlapping Long Peptides from a Tumor Self-Antigen and Poly-ICLC Shows Rapid Induction of Integrated Immune Response in Ovarian Cancer Patients," Clinical Cancer Research, 2012, 18(23):6497-6508.

Zhu et al., "Toll like receptor-3 ligand poly-ICLC promotes the efficacy of peripheral vaccinations with tumor antigen-derived peptide epitopes in murine CNS tumor models," Journal of Translational Medicine, Feb. 12, 2007, 5(10):15 pages.

O'Beirne et al., "Generation of functional CD8 T Cells by Human dendritic cells expressing glypican-3 epitopes," Journal of Experimental & Clinical Cancer Research, 2010, 29:48, 11 pages.

Office Action dated Sep. 1, 2020 in Chinese Application No. 201680014548.9, with English translation.

Sun et al., "Immune activity evaluation of GPC3 peptides recognized by HLA-A11 restricted T lymphocytes in hepatocellular carcinoma patients," Beijing Medical Journal, Dec. 31, 2014, 36(9):752-755.

Tada et al., "Analysis of cytotoxic T lymphocytes from a patient with hepatocellular carcinoma who showed a clinical response to vaccination with a glypican-3-derived peptide," International Journal of Oncology, Dec. 31, 2013, 43:1019-1026.

SEQUENCE LISTING

```
<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Met Val Asn Glu Leu Phe Asp Ser Leu
1               5

<210> SEQ ID NO 2
<211> LENGTH: 9
<212> TYPE: PRT
<213> ORGANISM: Homo sapiens

<400> SEQUENCE: 2

Leu Phe Asp Ser Leu Phe Pro Val Ile
1               5

<210> SEQ ID NO 3
<211> LENGTH: 9
<212> TYPE: PRT
<213> ORGANISM: Homo sapiens

<400> SEQUENCE: 3

Ser Ala Leu Asp Ile Asn Glu Cys Leu
1               5

<210> SEQ ID NO 4
<211> LENGTH: 9
<212> TYPE: PRT
<213> ORGANISM: Homo sapiens

<400> SEQUENCE: 4

Ser Leu Gln Val Thr Arg Ile Phe Leu
1               5

<210> SEQ ID NO 5
```

```
<211> LENGTH: 9
<212> TYPE: PRT
<213> ORGANISM: Homo sapiens

<400> SEQUENCE: 5

Ser Leu Thr Pro Gln Ala Phe Glu Phe
1               5

<210> SEQ ID NO 6
<211> LENGTH: 9
<212> TYPE: PRT
<213> ORGANISM: Homo sapiens

<400> SEQUENCE: 6

Gly Tyr Ile Cys Ser His Ser Pro Val
1               5

<210> SEQ ID NO 7
<211> LENGTH: 9
<212> TYPE: PRT
<213> ORGANISM: Homo sapiens

<400> SEQUENCE: 7

Ala Leu Asn Leu Gly Ile Glu Val Ile
1               5

<210> SEQ ID NO 8
<211> LENGTH: 9
<212> TYPE: PRT
<213> ORGANISM: Homo sapiens

<400> SEQUENCE: 8

Leu Leu Gln Ser Ala Ser Met Glu Leu
1               5

<210> SEQ ID NO 9
<211> LENGTH: 9
<212> TYPE: PRT
<213> ORGANISM: Homo sapiens

<400> SEQUENCE: 9

Lys Leu Thr Thr Thr Ile Gly Lys Leu
1               5

<210> SEQ ID NO 10
<211> LENGTH: 9
<212> TYPE: PRT
<213> ORGANISM: Homo sapiens

<400> SEQUENCE: 10

Gly Met Ile Lys Val Lys Asn Gln Leu
1               5

<210> SEQ ID NO 11
<211> LENGTH: 9
<212> TYPE: PRT
<213> ORGANISM: Homo sapiens

<400> SEQUENCE: 11

Ala Arg Leu Asn Met Glu Gln Leu Leu
1               5

<210> SEQ ID NO 12
<211> LENGTH: 580
<212> TYPE: PRT
```

-continued

<213> ORGANISM: Homo sapiens

<400> SEQUENCE: 12

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400
```

```
Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 13
<211> LENGTH: 9
<212> TYPE: PRT
<213> ORGANISM: Epstein-Barr virus

<400> SEQUENCE: 13

Thr Tyr Gly Pro Val Phe Met Cys Leu
1               5

<210> SEQ ID NO 14
<211> LENGTH: 9
<212> TYPE: PRT
<213> ORGANISM: Human immunodeficiency virus

<400> SEQUENCE: 14

Arg Tyr Leu Arg Asp Gln Gln Leu Leu
1               5

<210> SEQ ID NO 15
<211> LENGTH: 9
<212> TYPE: PRT
<213> ORGANISM: Influenza A virus

<400> SEQUENCE: 15

Gly Ile Leu Gly Phe Val Phe Thr Leu
1               5

<210> SEQ ID NO 16
<211> LENGTH: 9
<212> TYPE: PRT
<213> ORGANISM: Human immunodeficiency virus

<400> SEQUENCE: 16

Ser Leu Tyr Asn Thr Val Ala Thr Leu
1               5
```

```
<210> SEQ ID NO 17
<211> LENGTH: 9
<212> TYPE: PRT
<213> ORGANISM: Epstein-Barr virus

<400> SEQUENCE: 17

Leu Thr Ala Gly Phe Leu Ile Phe Leu
1               5

<210> SEQ ID NO 18
<211> LENGTH: 9
<212> TYPE: PRT
<213> ORGANISM: Human immunodeficiency virus

<400> SEQUENCE: 18

Ala Thr Leu Glu Glu Met Met Thr Ala
1               5
```

PEPTIDE DERIVED FROM GPC3, PHARMACEUTICAL COMPOSITION FOR TREATMENT OR PREVENTION OF CANCER USING SAME, IMMUNITY INDUCER, AND METHOD FOR PRODUCING ANTIGEN-PRESENTING CELLS

CROSS-REFERENCE TO RELATED APPLICATIONS

This application is a Divisional of U.S. application Ser. No. 16/185,734, filed Nov. 9, 2018, which is a Divisional of U.S. application Ser. No. 15/556,694, which is the U.S. National Stage application of PCT/JP2016/057356, filed Mar. 9, 2016, which claims priority from Japanese application JP 2015-046463, filed Mar. 9, 2015.

The instant application contains a Sequence Listing which has been submitted in ASCII format via EFS-WEB and is hereby incorporated by reference in its entirety. Said ASCII copy, created on Jan. 31, 2020, is named sequence.txt and is 8,100 bytes.

TECHNICAL FIELD

The present invention relates to a GPC3-derived peptide, more specifically an immunogenic peptide for presenting an antigen to a T cell via binding to a human leukocyte antigen, a pharmaceutical composition for treating or preventing cancer using the same, an immunity inducer, a method for producing an antigen-presenting cell, and the like.

BACKGROUND ART

Although it is considered that cancer cells always incidentally appear in a living body, it is hypothesized that the reaction by natural immunity normally occurs for elimination of a specific cancer antigen derived from cancer cells and that then a specific immune response is induced to cause the reaction of elimination of cancer cells by lymphocytes and other cells.

The recognition of a cancer cell-derived antigen requires the formation of a complex by a human leukocyte antigen (HLA) present on the cell surface and a lymphocyte. The HLA molecule as a major histocompatibility antigen is roughly divided into class I molecules (HLA types A, B, and C) and class II molecules (HLA types DP, DQ, and DR). The reaction of elimination of a cancer cell by a cytotoxic T cell (CTL) is induced by the specific recognition of a cancer antigen (CTL epitope) consisting of 8 to 11 amino acids which is presented on an HLA class I molecule on the cancer cell surface by a T cell antigen receptor (TCR) on the CTL.

The search for immunogenic peptides has been currently carried out with a view to their application to the treatment or prevention of various immune-related diseases; for example, Japanese Patent Laid-Open No. 08-151396 discloses that an oligopeptide consisting of a particular amino acid sequence has a HLA-binding capacity.

CITATION LIST

Patent Literature

Patent Literature 1: Japanese Patent Laid-Open No. 08-151396

SUMMARY OF INVENTION

Technical Problem

Many peptides having an HLA-binding capacity are known; however, there is further a need for peptides capable of being used for the treatment or prevention of various cancers. Since HLA gene is rich in polymorphism, there is also a need for multi-type immunogenic peptides each adaptable to a plurality of HLA types.

Solution to Problem

In view of the above-described circumstances, the present invention has an object of providing an immunogenic peptide capable of binding to an HLA class I molecule, particularly a peptide capable of inducing CTL, a pharmaceutical composition for treating or preventing cancer using the peptide, an immunity inducer, and a method for producing an antigen-presenting cell.

Specifically, the present invention includes the following inventions.

(1) A peptide comprising 8 or more consecutive amino acid residues in an amino acid sequence of any of SEQ ID NOS: 1 to 11 and consisting of 11 or less amino acid residues.

(2) The peptide according to (1), wherein in the amino acid sequence, 1 or several amino acids are substituted, inserted, deleted, or added, and the peptide has immunogenicity.

(3) The peptide according to (2), wherein in the amino acid sequence, the amino acid at position 2 is substituted by tyrosine, phenylalanine, methionine, tryptophan, valine, leucine, or glutamine, and/or the amino acid at the C-terminal is substituted by phenylalanine, leucine, isoleucine, tryptophan, methionine, or valine.

(4) A pharmaceutical composition for treating or preventing cancer, comprising the peptide according to any one of (1) to (3).

(5) The pharmaceutical composition according to (4), wherein the composition is in the form of a vaccine.

(6) The pharmaceutical composition according to (4) or (5), wherein the peptide can bind to one or more types of HLA molecules.

(7) An immunity inducer, comprising the peptide according to any one of (1) to (3).

(8) The immunity inducer according to (7), wherein the inducer is for inducing a cytotoxic T cell.

(9) The immunity inducer according to (7) or (8), wherein the peptide can bind to one or more types of HLA molecules.

(10) A method for producing an antigen-presenting cell having a CTL-inducing activity, comprising a step of contacting the peptide according to any one of (1) to (3) with an antigen-presenting cell in vitro.

Advantageous Effects of Invention

Attention has been given in recent years to immunotherapy as a method for treating cancer. The peptide of the present invention is strongly expected to have usefulness as a cancer vaccine because of its high HLA-binding capacity and also its high CTL-inducing capability. Its applications to various immunotherapies, particularly dendritic cell therapy, are also envisioned.

Glypican-3 (GPC3) is a protein belonging to the Glypican family. Glypican is one of proteoglycans and is known to bind to glycosyl-phosphatidylinositol on the cell surface.

Glypican controls the activity of various cell growth factors including Wnts, and the action is believed to be due to acceleration or inhibition of interactions between the cell growth factors and the receptors by Glypican. In particular, it has been revealed that GPC3 is expressed in almost all cases of hepatocellular carcinoma (HCC), and, on the other hand, is hardly expressed in normal liver, hepatic cirrhosis, and so on. Further, GPC3 is known to be highly expressed, not only in hepatocellular carcinoma, but also in melanoma, ovarian cancer, and so on.

1. "Glypican-3: a marker and a therapeutic target in hepatocellular carcinoma." Jorge Filmus and *Mariana* Capurro, FEBS J., 280: 2471-2476, 2013.
2. "Glypican-3: a new target for cancer immunotherapy." Mitchell Ho and Heungnam Kim, Eur. J. Cancer, 47, 333-338, 2011.

For hepatocellular carcinoma, clinical researches for a cancer vaccine with a GPC3-derived peptide which is highly expressed in hepatocellular carcinoma cells have been previously conducted, and the safety and immunity-inducing ability have been reported.

3. "Peptide vaccines for hepatocellular carcinoma." Daisuke Nobuoka, Toshiaki Yoshikawa, Yu Sawada, Toshiyoshi Fujiwara and Tetsuya Nakatsura, Human Vaccines & Immunotherapeutics, 9, 210-212, 2013.
4. "Phase I Trial of a Glypican-3-Derived Peptide Vaccine for Advanced Hepatocellular Carcinoma: Immunologic Evidence and Potential of Improving Overall Survival." Yu Sawada, et. al., Clin. Cancer. Res., 18, 3636-3696, 2012.

In the present invention, several peptides have been identified each of which is a GPC3-derived peptide different from any of the peptides reported in the clinical researches, and binds to an HLA molecule and has an immunity-inducing ability. Among the peptides of the present invention, a particular peptide can bind to a plurality of HLA types. Thus, the peptide of the present invention enables, for example, the provision of a cancer vaccine and dendritic cell therapy covering an extremely wide range of cancer patients.

DESCRIPTION OF EMBODIMENTS

1. Immunogenic Peptide

Figure 1:
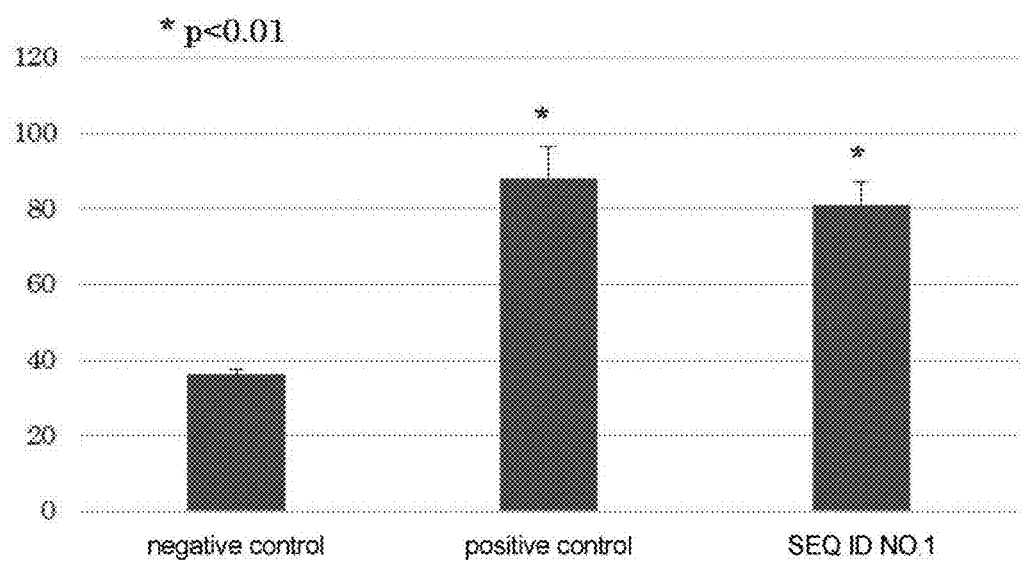
FIG. 1 is a graph showing the results of ELISPOT assay (the number of IFN-γ-producing cells) when samples derived from patients [0] (HLA type: 24: 02/24:02) having received HSP70 dendritic cell therapy were stimulated with the peptide of SEQ ID NO: 1.

The peptides according to the present invention are each a peptide comprising 8 or more consecutive amino acid residues in an amino acid sequence of any of SEQ ID NOS: 1 to 11 and consisting of 11 or less, preferably 10 or less, more preferably 9 or less amino acid residues in total. The peptide of the present invention may be a peptide consisting of an amino acid sequence of any of SEQ ID NOS: 1 to 11. The peptide of the present invention is derived from GPC3, which is one of Glypican. An amino acid sequence whose binding capacity to the HLA molecule is 3 or more in terms of a −log Kd value has been selected, and the binding capacity here was predicted by the hypothesis obtained using an active learning experiment method (Japanese Patent Laid-Open No. 08-151396) based on the amino acid sequence constituting GPC3.

The amino acid sequence constituting each peptide of the present invention and its HLA-binding prediction score are shown in Table 1 below.

TABLE 1

| Amino Acid Sequence (SEQ ID NO:) | Position in GPC3 | Binding Prediction Score | | |
|---|---|---|---|---|
| | | To A*24:02 | To A*02:01 | To A*02:06 |
| MVNELFDSL (SEQ ID NO: 1) | 166 | 4.9889 | 4.5125 | 4.914 |
| LFDSLFPVI (SEQ ID NO: 2) | 170 | 5.3875 | 4.6623 | 4.8693 |
| SALDINECL (SEQ ID NO: 3) | 190 | 5.0802 | 5.1752 | 4.9393 |

TABLE 1-continued

| Amino Acid Sequence (SEQ ID NO:) | Position in GPC3 | Binding Prediction Score | | |
|---|---|---|---|---|
| | | To A*24:02 | To A*02:01 | To A*02:06 |
| SLQVTRIFL (SEQ ID NO: 4) | 222 | 4.9563 | 4.7937 | 4.9102 |
| SLTPQAFEF (SEQ ID NO: 5) | 136 | 5.3611 | 4.4718 | 4.5358 |
| GYICSHSPV (SEQ ID NO: 6) | 407 | 5.2631 | 4.5208 | 4.6902 |
| ALNLGIEVI (SEQ ID NO: 7) | 232 | 4.7512 | 4.8916 | 4.8959 |
| LLQSASMEL (SEQ ID NO: 8) | 92 | 4.6163 | 4.9287 | 5.0213 |
| KLTTTIGKL (SEQ ID NO: 9) | 340 | 5.6526 | 4.2118 | 4.2929 |
| GMIKVKNQL (SEQ ID NO: 10) | 512 | 5.5052 | 4.3292 | 4.0995 |
| ARLNMEQLL (SEQ ID NO: 11) | 85 | 5.0076 | 4.1008 | 4.2227 |

The peptide of the present invention has an HLA-binding capacity and has immunogenicity (hereinafter sometimes simply referred to as "HLA peptide" or "immunogenic peptide"). As used herein, "immunogenicity" means the ability to induce an immune response and, for example, means having a CTL-inducing activity and consequently having a cytotoxic activity against cancer cells.

In a preferred embodiment, the peptide of the present invention is a multi-HLA peptide capable of binding to a plurality of allelotypes of HLA-A gene A. For example, the peptide of SEQ ID NO: 7 strongly binds to a product of HLA-A*24:02 gene (an HLA-A*24:02 molecule), a product of HLA-A*02:01 gene (an HLA-A*02:01 molecule), and a product of HLA-A*02:06 gene (an HLA-A*02:06 molecule), and has high immunogenicity.

The HLA subtype to which the peptide of the present invention can bind is not limited to HLA-A*24:02, HLA-A*02:01, or HLA-A*02:06. However, these HLA subtypes cover the order of 85% of oriental people including the Japanese and on the order of 55% of western people; thus, it is considered that the multi-HLA peptide of the present invention achieves a broad patient coverage, for example, in immunotherapy.

The peptide of the present invention may be modified in the amino acid residues constituting the amino acid sequence of any of SEQ ID NOS: 1 to 11 or a part thereof as long as it retains immunogenicity. The amino acid sequence of each of SEQ ID NOS: 1 to 11 intends a state which is presented on an antigen-presenting cell; however, when the peptide of the present invention is directly administered into the body, the peptide sometimes experiences changes, such as the digestion of its terminal in digestive organs and the like, depending on the administration route. Thus, before incorporation into an antigen-presenting cell, the peptide of the present invention may be present in the form of a precursor which is formed by adding one or more amino acid residues or the like at the N-terminal and/or C-terminal so that amino acid sequence of any of SEQ ID NOS: 1 to 11 are retained upon binding to a predetermined HLA class I molecule on the antigen-presenting cell.

In addition, the peptide of the present invention may have 1 or several amino acid residues constituting the peptide of the present invention substituted, inserted, deleted, or added, and/or have modifications, such as sugar chain addition, side chain oxidation, and/or phosphorylation, as long as the peptide has desired immunogenicity. "Amino acid" herein is used in its most comprehensive sense and includes artificial amino acid variants and derivatives in addition to natural amino acids. Examples of the amino acid herein include natural protein L-amino acids; D-amino acids; chemically modified amino acids, such as amino acid variants and derivatives; natural non-protein amino acids, such as norleucine, β-alanine, and ornithine; and chemically synthesized compounds having properties known in the art, characteristic of amino acids. Examples of the non-natural amino acid include α-methyl amino acids (e.g., α-methylalanine), D-amino acids, histidine-like amino acids (e.g., β-hydroxy-histidine, homohistidine, α-fluoromethyl-histidine, and α-methyl-histidine), amino acids having extra methylene on the side chain ("homo" amino acids), and amino acids in each of which the carboxylic acid functional group on the side chain is substituted by a sulfonic acid group (e.g., cysteic acid).

For the substitution of an amino acid residue, and the like, in consideration of the regularity of a peptide sequence having a binding capacity to HLA (J. Immunol., 152: p 3913, 1994; Immunogenetics, 41: p 178, 1995; J. Immunol., 155: p 4307, 1994), those skilled in the art can properly substitute an amino acid residue as a constituent of the peptide of the present invention.

More specifically, in the case of a peptide binding to an HLA-A*24:02 molecule, the amino acid at position 2 of the peptide may be substituted by tyrosine, phenylalanine, methionine, or tryptophan, and/or the C-terminal amino acid may be substituted by phenylalanine, leucine, isoleucine, tryptophan, or methionine. In the case of a peptide binding to an HLA-A*02:01 molecule, the amino acid at position 2 may be substituted by leucine or methionine, and/or the C-terminal amino acid may be substituted by valine or leucine. In addition, in the case of a peptide binding to an HLA-A*02:06 molecule, the amino acid at position 2 may be substituted by valine or glutamine, and/or the C-terminal amino acid may be substituted by valine or leucine.

Each peptide of the present invention can be produced using a technique known to those skilled in the art. For example, it may be artificially synthesized by a solid-phase method, such as the Fmoc method or the tBoc method, or a liquid-phase method. A desired peptide may also be produced by expressing a polynucleotide encoding the peptide of the present invention or a recombinant vector containing the polynucleotide. The peptides thus obtained can each be identified using a technique known to those skilled in the art. For example, it can be identified using the Edman degradation method or a mass spectrometry method.

2. Pharmaceutical Composition

The pharmaceutical composition for treating or preventing cancer according to the present invention contains, as an active ingredient, for example, a peptide containing 8 or more consecutive amino acid residues in one or more amino acid sequences selected from the group consisting of SEQ ID NOS: 1 to 11 and consisting of 11 or less, preferably 10 or less, more preferably 9 or less amino acid residues in total. The peptide contained in the pharmaceutical composition may be a peptide consisting of an amino acid sequence of any of SEQ ID NOS: 1 to 11. The peptide is as defined hereinbefore.

The peptide of the present invention induces CTL by being presented on an antigen-presenting cell, and the induced CTL injures a cancer cell. Thus, the active ingredient of the pharmaceutical composition of the present invention is not limited to the peptide of the present invention, and may be a component capable of directly or indirectly inducing CTL, for example, a polynucleotide encoding the peptide or a vector containing the polynucleotide, or an antigen-presenting cell presenting a complex of the peptide and an HLA molecule on the surface or an exosome secreted from the antigen-presenting cell, or a combination thereof. Examples of the antigen-presenting cell used include a macrophage and a dendritic cell; however, it is preferable to use the dendritic cell, which has a high CTL-inducing capability. Any of other ingredients known to be used for cancer therapy, such as a chemokine, a cytokine, a tumor necrosis factor, and a chemotherapeutic agent, may be contained in the pharmaceutical composition of the present invention. The dose of the peptide may be, for example, about 1 to 10 mg per day when the patient is an adult. However, the dose varies depending on the age and body weight of the patient, the administration method, and the like, and thus is properly determined by those skilled in the art.

The pharmaceutical composition of the present invention is thought to be useful for the killing of cancer cells by, for example, but not intended to be limited to, the following action mechanism. The administration of the pharmaceutical composition of the present invention to a particular cancer patient results in that the peptide in the pharmaceutical composition is presented in a state in which it is bound to an HLA molecule on the antigen-presenting cell surface. On recognizing the peptide on such an antigen-presenting cell, CTL is activated, proliferated, and systemically circulated. When the peptide-specific CTL enters cancer tissue, it recognizes the same peptide derived from a specific cancer antigen, naturally binding to an HLA molecule present on the cancer cell surface to kill the cancer cell. Such an action contributes to the cancer treatment.

The pharmaceutical composition of the present invention can be used not only for treating cancer but also for preventing cancer. For example, the administration of the pharmaceutical composition of the present invention into a healthy human body induces CTL, and the induced cytotoxic T cell stay in the body and thus, when a particular cancer cell occurs, can injure the cancer cell. Similarly, the composition may be administered into a human body after treating cancer to prevent the recurrence of the cancer.

Any cancer expressing GPC3 is contemplated as a cancer to be treated or prevented. More specific examples of the cancer of interest include, but not intended to be limited to, hepatocellular cancer, cutaneous cancer such as melanoma, and ovarian cancer. For example, since GPC3 from which the peptide of the present invention is derived is overexpressed in hepatocellular cancer, it is considered that the peptide of the present invention is effective particularly in treating or preventing the hepatocellular cancer. When a plurality of cancers to be treated or prevented are present, a plurality of active ingredients, including the immunogenic peptide, may be contained in the pharmaceutical composition of the present invention.

The pharmaceutical composition of the present invention can be dissolved in an aqueous solvent, formulated in the form of a pharmaceutically acceptable salt, and administered to patients. Examples of the form of such a pharmaceutically acceptable salt include a form buffered at physiological PH in the form of a physiologically acceptable water-soluble salt, for example, a salt of sodium, potassium, magnesium, or calcium. In addition to the water-soluble solvent, a non-water-soluble solvent may also be used; examples of such a non-water-soluble solvent include alcohols, such as ethanol and propylene glycol.

The formulation containing the pharmaceutical composition of the present embodiment may contain agents for various purposes; examples of such agents include a preservative and a buffer agent. Examples of the preservative include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol, phenylethyl alcohol, ammonia, dithiothreitol, and beta-mercaptoethanol. Examples of the buffer agent include sodium carbonate, sodium borate, sodium phosphate, sodium acetate, and sodium bicarbonate. These agents can be present in an amount capable of maintaining the pH of a system at 2 to 9, preferably 4 to 8.

The dosage form of the pharmaceutical composition of the present invention is not particularly limited; however, when it is used in the form of a vaccine, examples of its dosage form include injections (intramuscular, subcutaneous, and intracutaneous), oral formulations, and nasal drop formulations. When the pharmaceutical composition of the present invention is in the form of a vaccine, it may be a mixed cocktail vaccine containing a plurality of active ingredients. For example, such a vaccine can contain any two or more of the peptides of SEQ ID NOS: 1 to 11, or contain a plurality of active ingredients by combination with other active ingredients.

The vaccine of the present invention may be an inert ingredient-containing vaccine containing an ingredient which is an ingredient other than the pharmaceutical composition, has no activity per se, and has the effect of further enhancing the effect of the pharmaceutical composition as a vaccine. Examples of the inert ingredient include an adjuvant and a toxoid. Examples of the adjuvant include, but not intended to be limited to, precipitation type ones, such as aluminium hydroxide, aluminium phosphate, and calcium phosphate, and oily type ones, such as Freund's complete adjuvant and Freund's incomplete adjuvant.

When present in the form of a vaccine, the pharmaceutical composition of the present invention is preferably administered into the body by injection or infusion, such as intracutaneous, subcutaneous, or intramuscular administration, or by dermal administration or inhalation through the mucosa of the nose, pharynx, or the like. Its single dose can be set to between a dose capable of significantly inducing cytotoxic T cells and a dose at which a significant number of non-cancer cells experience injury.

The pharmaceutical composition of the present invention is contemplated for not only administration to a human body but also extracorporeal use. More specifically, the pharmaceutical composition of the present invention may be used for the purpose of stimulating an antigen-presenting cell in vitro or ex vivo to increase its CTL-inducing activity. For example, in a case where the pharmaceutical composition of the present invention is used for dendritic cell therapy for cancer, the composition can be contacted with antigen-presenting cells, such as dendritic cells, derived from a patient in need of cancer treatment or prevention in advance, followed by administering the antigen-presenting cells to the patient by returning them into the patient's body. The peptide contained in the pharmaceutical composition can be introduced into an antigen-presenting cell, for example, by a lipofection method or an injection method. When a polynucleotide encoding the peptide of the present invention is used in such an application, the polynucleotide can be introduced into an antigen-presenting cell by a technique known in the art. For example, an antigen-presenting cell derived from a patient may be transformed in vitro using a polynucleotide of interest or a vector encoding the polynucleotide by a lipofection method, an electroporation method, a microinjection method, a cell fusion method, a DEAE dextran method, a calcium phosphate method, or the like.

3. Immunity Inducer

The immunity inducer according to the present invention contains, as an active ingredient, for example, a peptide containing 8 or more consecutive amino acid residues in one or more amino acid sequences selected from the group consisting of SEQ ID NOS: 1 to 11, and consisting of 11 or less, preferably 10 or less, more preferably 9 or less amino acid residues. The peptide contained in the immunity inducer may be a peptide consisting of an amino acid sequence of any of SEQ ID NOS: 1 to 11. The peptide is as defined hereinbefore.

It is considered that the peptide of the present invention induces immunity by being presented on an antigen-presenting cell. Thus, the active ingredient of the immunity inducer of the present invention is not limited to the peptide of the present invention, and may be a component capable of directly or indirectly inducing immunity, for example, a polynucleotide encoding the peptide of the present invention or an expression vector containing the peptide, or an antigen-presenting cell presenting a complex of the peptide and an HLA molecule on the surface or an exosome secreted from the antigen-presenting cell, or a combination thereof. Examples of the antigen-presenting cell used include a macrophage and a dendritic cell; however, it is preferable to use the dendritic cell, which has a high CTL-inducing capability.

The immunity inducer of the present invention is contemplated for not only administration to a human body but also extracorporeal use. More specifically, the immunity inducer of the present invention may be used for the purpose of stimulating an antigen-presenting cell in vitro or ex vivo to increase its CTL-inducing activity. For example, in a case where the immunity inducer of the present invention is used for dendritic cell therapy, the inducer can be contacted with antigen-presenting cells, such as dendritic cells, derived from a patient in need of immunity induction in advance, followed by administering the antigen-presenting cells to the patient by returning them into the patient's body. The peptide contained in the immunity inducer can be introduced into an antigen-presenting cell, for example, by transfection via a liposome (a lipofection method) or an injection method. When a polynucleotide encoding the peptide of the present invention is used in such an application, the polynucleotide can be introduced into an antigen-presenting cell by a technique known in the art. For example, an antigen-presenting cell derived from a patient may be transformed in vitro using a polynucleotide of interest or a vector expressing the polynucleotide by a lipofection method, an electroporation method, a microinjection method, a cell fusion method, a DEAE dextran method, a calcium phosphate method, or the like.

As used herein, "immunity induction" means inducing an immune response, for example, increasing the CTL-inducing activity of an antigen-presenting cell, and further increasing the cytotoxic activity of CTL against a cancer cell. As used herein, "CTL induction" means inducing or proliferating CTL specifically recognizing a certain antigen, or differentiating a naive T cell into an effector cell having the ability to kill a target cell (cytotoxic activity), such as a cancer cell, and/or increasing the cytotoxic activity of CTL by the presentation of the peptide of the present invention on the antigen-presenting cell surface in vitro or in vivo. The CTL-inducing activity can be measured by evaluating the production of cytokines (for example, interferon (IFN)-$\gamma$)) by CTL. For example, the CTL-inducing activity may be measured by evaluating an increase in cytokine-producing cells induced from precursor cells by antigen-presenting cells, such as peripheral-blood monocytes, stimulated with the peptide of the present invention, using a known high-sensitive immunoassay, such as ELISPOT (Enzyme-Linked ImmunoSpot) assay and ELISA (Enzyme-Linked ImmunoSorbent Assay). The cytotoxic activity can also be measured by a known method, such as a $^{51}$Cr release method. When the activity is significantly increased, for example, by 5% or more, 10% or more, 20% or more, preferably 50% or more, compared to control, immunity or CTL can be evaluated to have been induced.

4. Method for Producing Antigen-Presenting Cell

The method for producing an antigen-presenting cell according to the present invention includes a step of contacting, for example, a peptide containing 8 or more consecutive amino acid residues in one or more amino acid sequences selected from the group consisting of SEQ ID NOS: 1 to 11, and consisting of 11 or less, preferably 10 or less, more preferably 9 or less amino acid residues in total, with an antigen-presenting cell in vitro. The peptide used in the production method of the present invention may be a peptide consisting of an amino acid sequence of any of SEQ ID NOS: 1 to 11. The peptide is as defined hereinbefore.

It is considered that the peptide used in the production method of the present invention binds to an HLA class I molecule on the antigen-presenting cell surface, is presented to CTL as an antigen peptide, and thereby induces the CTL activity of the antigen-presenting cell. Thus, the component to be contacted with an antigen-presenting cell is not limited to the peptide of the present invention, and may be a component capable of directly or indirectly inducing CTL, for example, a polynucleotide encoding the peptide or a vector containing the polynucleotide, or an antigen-presenting cell presenting a complex of the peptide and an HLA molecule on the surface or an exosome secreted from the antigen-presenting cell, or a combination thereof. Examples of the antigen-presenting cell used include a macrophage and a dendritic cell; however, it is preferable to use the dendritic cell, which has a high CTL-inducing capability.

The antigen-presenting cell produced by the production method of the present invention is contemplated to be not only used as an active ingredient of the pharmaceutical composition or the immunity inducer but also used for immunotherapy and the like. For example, in a case where the antigen-presenting cells produced are used for dendritic cell therapy for cancer, the cells can be contacted with antigen-presenting cells, such as dendritic cells, having a low CTL-inducing capability, derived from a patient in need of immunity induction in advance, followed by administering the antigen-presenting cells to the patient by returning them into the patient's body. The peptide of the present invention can be introduced into an antigen-presenting cell, for example, by transfection via a liposome (a lipofection method) or an injection method. When a polynucleotide encoding the peptide of the present invention is used in such an application, the polynucleotide can be introduced into an antigen-presenting cell by a technique known in the art. For example, an antigen-presenting cell derived from a patient may be transformed in vitro using a polynucleotide of interest or a vector encoding the polynucleotide by a lipofection method, an electroporation method, a microinjection method, a cell fusion method, a DEAE dextran method, a calcium phosphate method, or the like.

Example 1

The present invention will be more specifically described below with reference to Examples. However, the present invention is not intended to be limited thereto.

Specifically, the procedures of prediction, experiment, and evaluation in this Example were carried out based on the active learning experiment design described in International Publication No. WO 2006/004182. A rule was constructed by repeating the following steps as a whole.

(1) A low rank learning algorithm to be described hereinafter is once tried. That is, a plurality of hypotheses are generated based on random resampling from accumulated data, and the point is chosen at which the variance of predicted values of randomly generated candidate query points (peptides) is largest as the query point to be experimented.

(2) The peptide at the chosen query point is produced by synthesis and purification methods to be described hereinafter. The actual binding capacity is measured by an experiment to be described hereinafter, and added to the accumulated data.

Performing such an active learning method could reduce the number of binding experiments which are otherwise necessary to carry out for all of 5 hundred billion ($=20^9$) or more candidate substances of HLA-binding peptides consisting of 9 amino acid residues.

Using the rule as described above, the amino acid sequences of SEQ ID NOS: 1 to 11 were extracted.
<Synthesis and Purification of Peptide>

The peptides having the amino acid sequences of SEQ ID NOS: 1 to 11 were manually synthesized by the Merrifield solid-phase method using Fmoc amino acids. The resultant were deprotected and then subjected to reverse-phase HPLC purification using a C18 column to a purity of 95% or more. The identification of the peptides and confirmation of the purity thereof were performed by MALDI-TOF mass spectrometry (AB SCIEX MALDI-TOF/TOF5800). Peptide quantification was carried out by Micro BCA assay (Thermo Scientific Co., Ltd.) using BSA as a standard protein.
<Binding Experiment of Peptide to HLA-A*24:02 Molecule>

The binding capacity of each peptide to the HLA-A*24:02 molecule as the product of HLA-A*24:02 gene was measured using C1R-A24 cells expressing the HLA-A*24:02 molecule (the cells prepared by Prof. Masafumi Takeguchi, Kumamoto University were gifted by Assoc. Prof. Masaki Yasukawa, Ehime University with permission).

First, C1R-A24 cells were exposed to acidic conditions of pH 3.3 for 30 seconds to dissociate and remove endogenous peptides which were originally bound to the HLA-A*24:02 molecule and a light chain, β2m, which was commonly associated with HLA class I molecules. After neutralization, purified β2m was added to the C1R-A24 cells, which was then added to peptide dilution series. The mixtures were each then incubated on ice for 4 hours. The 3-molecule assembly (MHC-pep) consisting of the HLA-A*24:02 molecule, the peptide, and β2 m which had been reasociated during the incubation was stained with a fluorescent labeled monoclonal antibody, 17A12, recognizing the assembly.

Subsequently, the number of MHC-pep's per C1R-A24 cell (which is proportional to the fluorescent intensity of the above fluorescent antibody) was quantitatively measured using a fluorescent cell analyzer, FACScan (Becton, Dickinson and Company). The binding dissociation constant, Kd value, between the HLA-A*24:02 molecule and the peptide was calculated from the average fluorescent intensity per cell using a method as published in a paper (Udaka et al., Immunogenetics, 51, 816-828, 2000) by the present inventor.
<Binding Experiment of Peptide to HLA-A*02:01 Molecule>

The binding capacity of each peptide to the HLA-A*02:01 molecule as the product of HLA-A*02:01 gene was measured using a cell line, T2, (purchased from ATCC) expressing the HLA-A*02:01 molecule.

T2 cells and purified β2m were added to stepwise dilution series of a peptide whose binding capacity was to be measured, which was then incubated at 37° C. for 4 hours. The HLA-A*02:01 molecule whose expression level was concentration-dependently increased by this time point was stained with an assembly-specific fluorescent labeled monoclonal antibody, BB7.2.

Thereafter, the amount of fluorescence per cell was measured using a flow cytometer, and the dissociation constant, Kd value, was calculated using a method as published in a paper by the present inventor (Udaka et al., Immunogenetics, 51, 816-828, 2000).
<Binding Experiment of Peptide to HLA-A*02:06 Molecule>

The binding capacity of each peptide to the HLA-A*02:06 molecule as the product of HLA-A*02:06 gene was measured using RA2.6 cells (a cell line newly prepared at Kochi University) in which cDNA of the HLA-A*02:06 gene was introduced into RMAS as a mouse TAP (transporter associated with antigen processing)-deficient cell line.

First, the RA2.6 cells were cultured overnight at 26° C. to accumulate the HLA-A*02:06 molecules unbound to the peptide on the cell surface. Any of peptide dilution series was added thereto for binding at 26° C. for 60 minutes.

Subsequently, the mixture was cultured at 35° C. for 4 hours, resulting in the denaturation of the empty HLA-A*02:06 molecule unbound to the peptide and the loss of its steric structure. A fluorescent labeled monoclonal antibody, BB7.2, specifically recognizing a peptide-bound HLA-A*02:06 molecule, was added thereto, which was then incubated on ice for 20 minutes to stain the cells.

Thereafter, the amount of fluorescence per cell was measured using a flow cytometer, and the dissociation constant, Kd value, was calculated using a method as published in a paper by the present inventor (Udaka et al., Immunogenetics, 51, 816-828, 2000).

<Evaluation Result of Binding Experiment>

As a result, the binding experiment data of the peptides of the present invention to each HLA molecule as shown in the following table were obtained.

(SEQ ID NOS: 1 to 11) were each added to 20 μg/ml. Then, the medium containing the dendritic cells was cultured at 37° C. for 2 hours. The following peptides were used as positive and negative controls.

Positive control for HLA-A*24:02 (EBV LMP2, 419-427: TYGPVFMCL (SEQ ID NO: 13))

Negative control for HLA-A*24:02 (HIV env gp160, 584-592: RYLRDQQLL (SEQ ID NO: 14))

Positive control for HLA-A*02:01 (Flu A MP, 58-66: GILGFVFTL (SEQ ID NO: 15))

Negative control for HLA-A*02:01 (HIV gap p17, 77-85: SLYNTVATL (SEQ ID NO: 16))

TABLE 2

| Amino Acid Sequence (SEQ ID NO:) | Position in GPC3 | Binding Experiment Data | | |
|---|---|---|---|---|
| | | To A*24:02 | To A*02:01 | To A*02:06 |
| MVNELFDSL (SEQ ID NO: 1) | 166 | -4.699595957 | -5.305836823 | -6.140220372 |
| LFDSLFPVI (SEQ ID NO: 2) | 170 | -7.427547379 | -5.06520602 | >-3 |
| SALDINECL (SEQ ID NO: 3) | 190 | >-3 | >-3 | -6.316321482 |
| SLQVTRIFL (SEQ ID NO: 4) | 222 | -5.336368455 | -6.210154227 | -5.213788842 |
| SLTPQAFEF (SEQ ID NO: 5) | 136 | -7.113561896 | -4.9256496 | -4.515516445 |
| GYICSHSPV (SEQ ID NO: 6) | 407 | -6.548090575 | >-3 | >-3 |
| ALNLGIEVI (SEQ ID NO: 7) | 232 | -3.956124763 | -5.917879215 | -4.161231756 |
| LLQSASMEL (SEQ ID NO: 8) | 92 | -5.48762276 | -6.136635191 | -5.877071673 |
| KLTTTIGKL (SEQ ID NO: 9) | 340 | -5.211802039 | -4.970696549 | -5.033936719 |
| GMIKVKNQL (SEQ ID NO: 10) | 512 | -6.904149343 | -4.757453097 | -3.357850496 |
| ARLNMEQLL (SEQ ID NO: 11) | 85 | -5.203320264 | -3.84036042 | -2.764152073 |

The amino acid sequences of SEQ ID NOS: 1 to 11 are derived from the full-length sequence of the predetermined genomic protein of GPC3 registered in GENBANK (SEQ ID NO: 12) (>gi|4758462|ref|NP_004475.1| glypican-3 isoform 2 precursor [*Homo sapiens*]).

<Immunity Induction Test of Peptide>

(1) Preparation of Peptide-Stimulated Dendritic Cell

Day 0 to 9 (Induction of Dendritic Cell)

Of peripheral blood monocytes obtained by pheresis from the patient [0] treated with HSP70 dendritic cell therapy, a cell fraction adhering to the culture flask was cultured in AIM-CM medium (trade name "Gibco" from Thermo Fisher Scientific Co., Ltd.) at 37° C. for 10 days. During culture, 15 μl of IL-4 and 30 μl of granulocyte-monocyte colony-stimulating factor (GM-CSF) were added to the medium at day 0 and day 3, and 15 μl of IL-4, 30 μl of GM-CSF, and 75 μl of tumor necrosis factor (TNF)-α were added at day 5.

Day 10 (Stimulation with Peptide and Recovery of Dendritic Cell)

The dendritic cells induced were newly recovered into AIM-CM medium, and the peptides of the present invention Positive control for HLA-A*02:06 (EBV LMP2 453-461: LTAGFLIFL (SEQ ID NO: 17))

Negative control for HLA-A*02:06 (HIV gap p24 341-349: ATLEEMMTA (SEQ ID NO: 18))

The dendritic cells were recovered, washed 3 times or more with a sufficient amount of AIM-CM medium, and counted.

(2) Preparation of CD8T Cell

Day 0 to 9

Of peripheral blood monocytes obtained by pheresis from the patient treated 2 times or more with the above vaccine, a floating cell fraction (including lymphocytes) not adhering to the culture flask was cultured in AIM-CM medium (from GIBCO Co., Ltd.) at 37° C. for 10 days. During culture, 40 μl of IL-2 was added to the medium at day 4 and day 6.

Day 10

Using CD8 Negative Selection Kit (from Miltenyi Biotec), CD8T cells were separated from the medium and counted.

(3) Coculture

The dendritic cells and the CD8T cells obtained in (1) and (2) above were cocultured in AIM medium at 37° C. under the following conditions.

CD8T cells: 5×10³ cells/well
Dendritic cells: 2×10³ cells/well
Day 12 or 13

To the above medium was added 0.4 ml/well of AIM-CM medium containing IL-2 in an amount of 20 U/ml.

(4) ELISPOT Assay

Day 17

The CD8T cells were added to a 96-well plate for ELISPOT (from Millipore), coated with an anti-TFN-γ monoclonal antibody (from Mabtech AB) to 2×10⁴ cells/well. For each sample, 3 or more wells were used. To each well was added 100 μl of AIM-V (from trade name "Gibco" from Thermo Fisher Scientific Co., Ltd.). The 96-well plate for ELISPOT was cultured at 37° C.

Day 18

Figure 2:
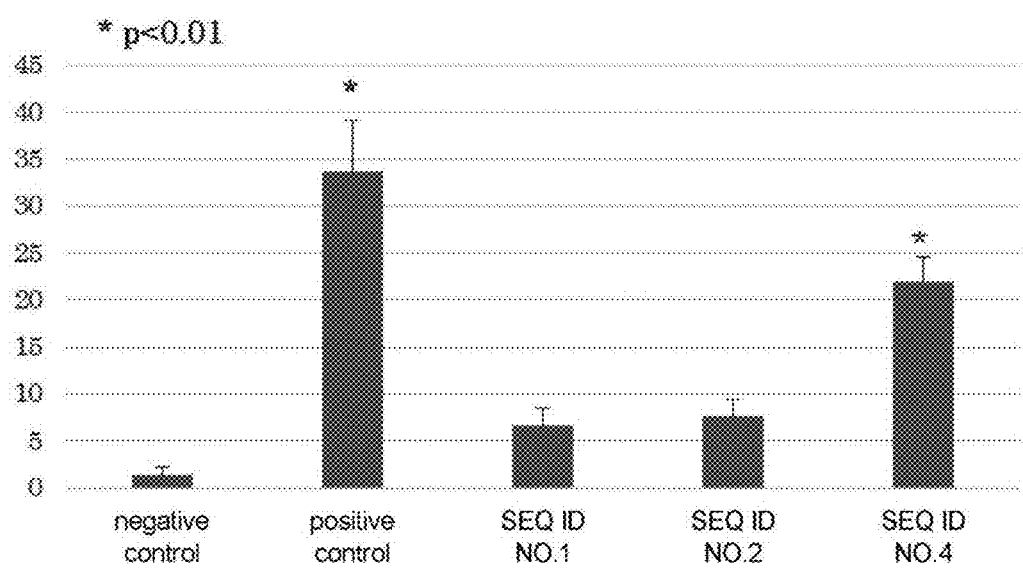
FIG. 2 is a graph showing the results of ELISPOT assay (the number of IFN-γ-producing cells) when samples derived from patients (HLA type: 02: 01/24:02) having received HSP70 dendritic cell therapy were stimulated with the peptide of SEQ ID NO: 1, 2, or 4.
Figure 3:
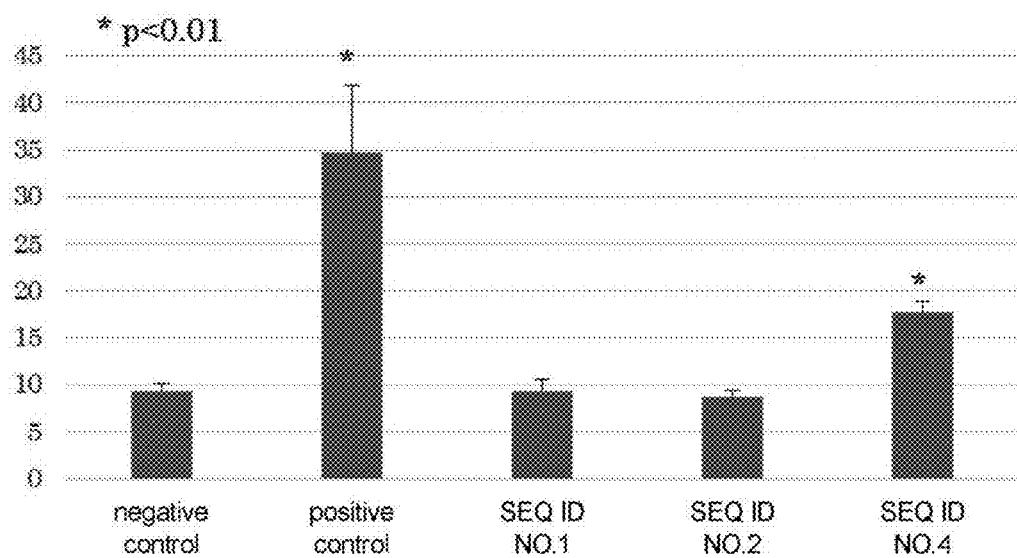
FIG. 3 is a graph showing the results of ELISPOT assay (the number of IFN-γ-producing cells) when samples derived from patients (HLA type: 02: 01/33:03) having received HSP70 dendritic cell therapy were stimulated with the peptide of SEQ ID NO: 1, 2, or 4.
Figure 4:
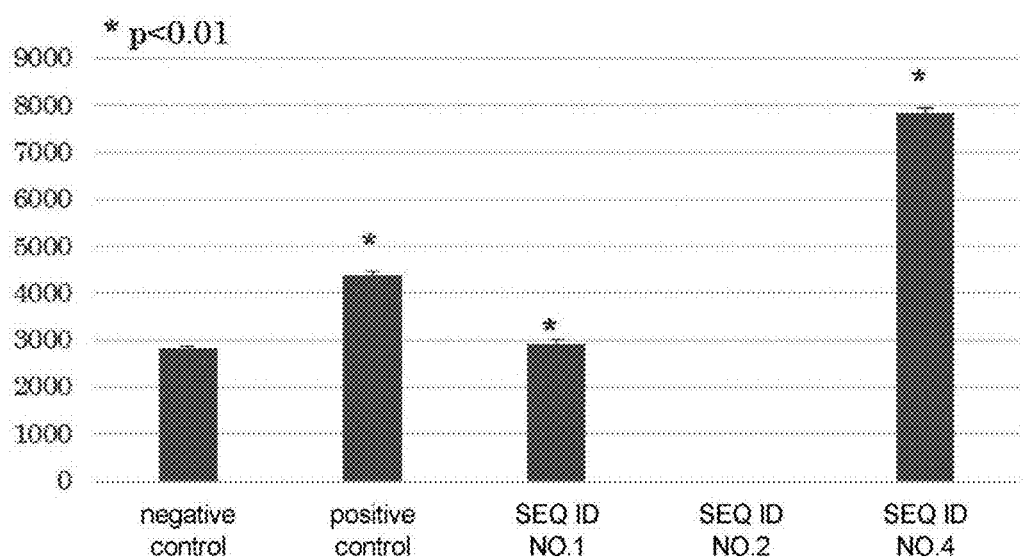
FIG. 4 is a graph showing the results of ELISA assay (the number of IFN-γ-producing cells) when samples derived from patients (HLA type: 24: 02/26:01) having received HSP70 dendritic cell therapy were stimulated with the peptide of SEQ ID NO: 1, 2, or 4.
Figure 5:
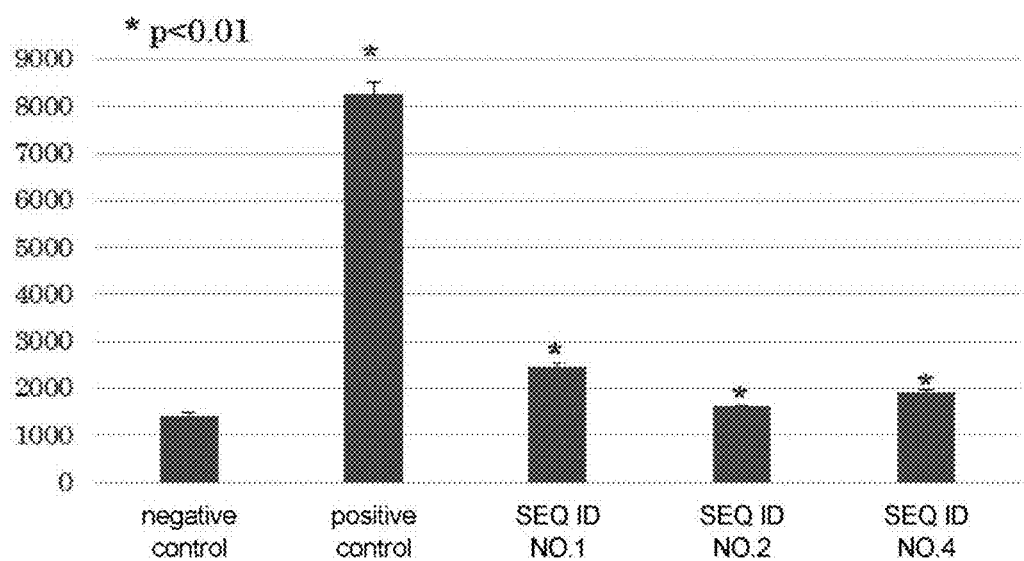
FIG. 5 is a graph showing the results of ELISA assay (the number of IFN-γ-producing cells) when samples derived from patients (HLA type: 24: 02/24:02) having received HSP70 dendritic cell therapy were stimulated with the peptide of SEQ ID NO: 1, 2, or 4.
Figure 6:
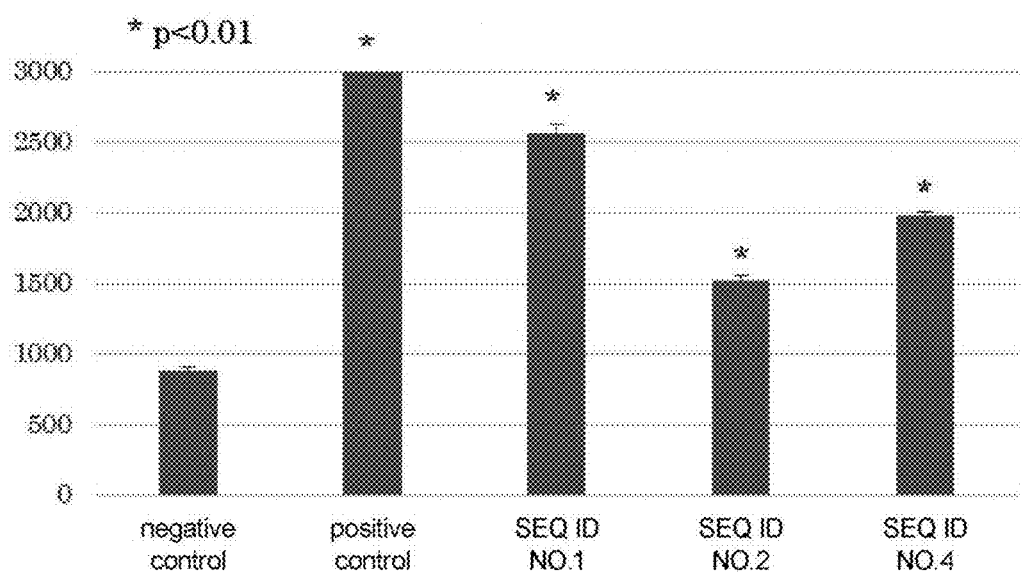
FIG. 6 is a graph showing the results of ELISA assay (the number of IFN-γ-producing cells) when samples derived from patients (HLA type: 11: 01/24:02) having received HSP70 dendritic cell therapy were stimulated with the peptide of SEQ ID NO: 1, 2, or 4.
Figure 7:
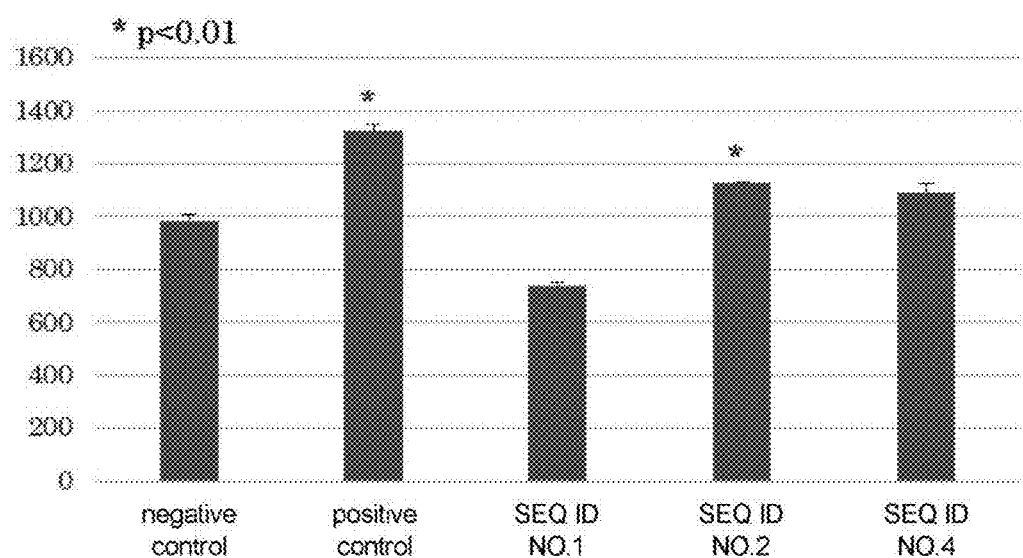
FIG. 7 is a graph showing the results of ELISA assay (the number of IFN-γ-producing cells) when samples derived from patients (HLA type: 02: 01/24:02) having received HSP70 dendritic cell therapy were stimulated with the peptide of SEQ ID NO: 1, 2, or 4.
Figure 8:
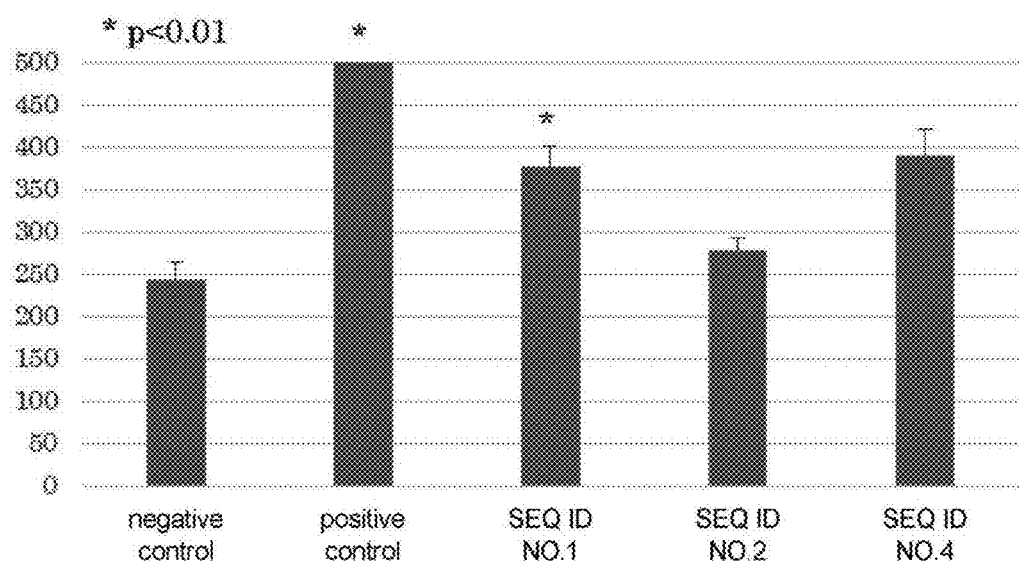
FIG. 8 is a graph showing the results of ELISA assay (the number of IFN-γ-producing cells) when samples derived from patients (HLA type: 02: 01/33:03) having received HSP70 dendritic cell therapy were stimulated with the peptide of SEQ ID NO: 1, 2, or 4.

The anti-TFN-γ antibody was added to each well and further reacted with an HRP enzyme-labeled secondary antibody to measure the number of IFN-γ-producing cells by color reaction. As typical results of the ELISPOT assay, those for patients whose HLA type was 24:02/24:02 are shown in FIG. 1; those for patients, 02:01/24:02, in FIG. 2; and those for patients, 02:01/33:03, in FIG. 3. In each figure, the average of 3 assay results are indicated.

(5) ELISA Assay

Day 17

A culture supernatant at day 7 after coculture of T cells with dendritic cells pulsed with each of the above peptides was diluted to the 4 levels of ×1, ×5, ×25, and ×125 to identify the dilution level falling within the limit of measurement using Human IFN-γ ELISA MAX Deluxe Set (from BioLegend Inc.). Thereafter, each sample was measured 3 times at the identified dilution level. As typical results of the ELISA assay, those for patients whose HLA type was 24:02/26:01, those for patients whose HLA type was 24:02/24:02, those for patients whose HLA type was 11:01/24:02, those for patients whose HLA type was 02:01/24:02, and those for patients whose HLA type was 02:01/33:03, are shown in FIGS. 4 to 8 respectively.

The present invention has been described above based on Example. This Example is merely illustrative, and it should be understood by those skilled in the art that various modifications may be made and that the modifications are also within the scope of the present invention.

The invention claimed is:

1. A peptide comprising 8 or more consecutive amino acid residues but 11 or less amino acid residues of SEQ ID NO: 4.

2. A pharmaceutical composition for treating or preventing cancer, comprising the peptide according to claim 1.

3. The pharmaceutical composition according to claim 2, wherein the composition is in the form of a vaccine.

4. The pharmaceutical composition according to claim 3, wherein the peptide can bind to one or more types of HLA molecules.

5. An immunity inducer, comprising the peptide according to claim 1.

6. The immunity inducer according to claim 5, wherein the inducer is for inducing a cytotoxic T cell.

7. The immunity inducer according to claim 6, wherein the peptide can bind to one or more types of HLA molecules.

8. A method for producing an antigen-presenting cell having CTL-inducing activity, comprising a step of contacting the peptide according to claim 1 with an antigen-presenting cell in vitro.

* * * * *